(12) United States Patent
Wong et al.

(10) Patent No.: US 7,358,489 B2
(45) Date of Patent: Apr. 15, 2008

(54) ULTRA LOW COST NDIR GAS SENSORS

(75) Inventors: Jacob Y. Wong, Goleta, CA (US); Chi Wai Tse, Hong Kong SAR (CN)

(73) Assignee: Airware, Inc., Goleta, CA (US)

( * ) Notice: Subject to any disclaimer, the term of this patent is extended or adjusted under 35 U.S.C. 154(b) by 271 days.

(21) Appl. No.: 11/197,790

(22) Filed: Aug. 4, 2005

(65) Prior Publication Data

US 2007/0029487 A1 Feb. 8, 2007

(51) Int. Cl.
*H01J 49/00* (2006.01)
*G01J 5/02* (2006.01)

(52) U.S. Cl. .................................. 250/300; 250/339.13
(58) Field of Classification Search ................ 250/300, 250/339.13
See application file for complete search history.

(56) References Cited

U.S. PATENT DOCUMENTS

| | | | |
|---|---|---|---|
| 5,026,992 A | 6/1991 | Wong | |
| 5,163,332 A | 11/1992 | Wong | |
| 5,222,389 A | 6/1993 | Wong | |
| 5,341,214 A | 8/1993 | Wong | |
| 5,347,474 A | 9/1994 | Wong | |
| 5,453,621 A | 9/1995 | Wong | |
| 5,464,983 A * | 11/1995 | Wang | 250/343 |
| 5,502,308 A | 3/1996 | Wong | |
| 5,747,808 A | 5/1998 | Wong | |
| 5,834,777 A | 11/1998 | Wong | |
| 6,107,925 A * | 8/2000 | Wong | 340/628 |
| 6,237,575 B1 | 5/2001 | Lambert et al. | |

* cited by examiner

*Primary Examiner*—David P. Porta
*Assistant Examiner*—Mindy Vu
(74) *Attorney, Agent, or Firm*—Wagner, Anderson & Bright, LLP; Roy L. Anderson

(57) ABSTRACT

The concentration of a gas species is detected by using a single beam NDIR gas sensor in which an infrared source element is driven at two different temperatures, a feed back loop senses an operation voltage of the source, a differential gain amplifier creates a high cycle amplified output during a high cycle and a low cycle amplified output during a low cycle while a controller synchronizes the source driver so that a signal processor can determine the gas concentration through use of the high cycle amplified output and the low cycle amplified output. The infrared source can be a non-genuine blackbody source such as an incandescent miniature light bulb when the sample chamber is a thermally insulated aluminum tube that is maintained at a preselected temperature greater than ambient so that the glass envelope of the bulb is maintained at an equilibrium temperature (such as approximately 30 degrees Celsius plus or minus two degrees Celsius) during its low cycle operation state.

18 Claims, 5 Drawing Sheets

A schematic circuit illustrating the control of the radiation source via the synchronization of the detected high and low signals by the microprocessor in one 'AC' cycle using the multi-channel Analog-to-Digital converter chip.

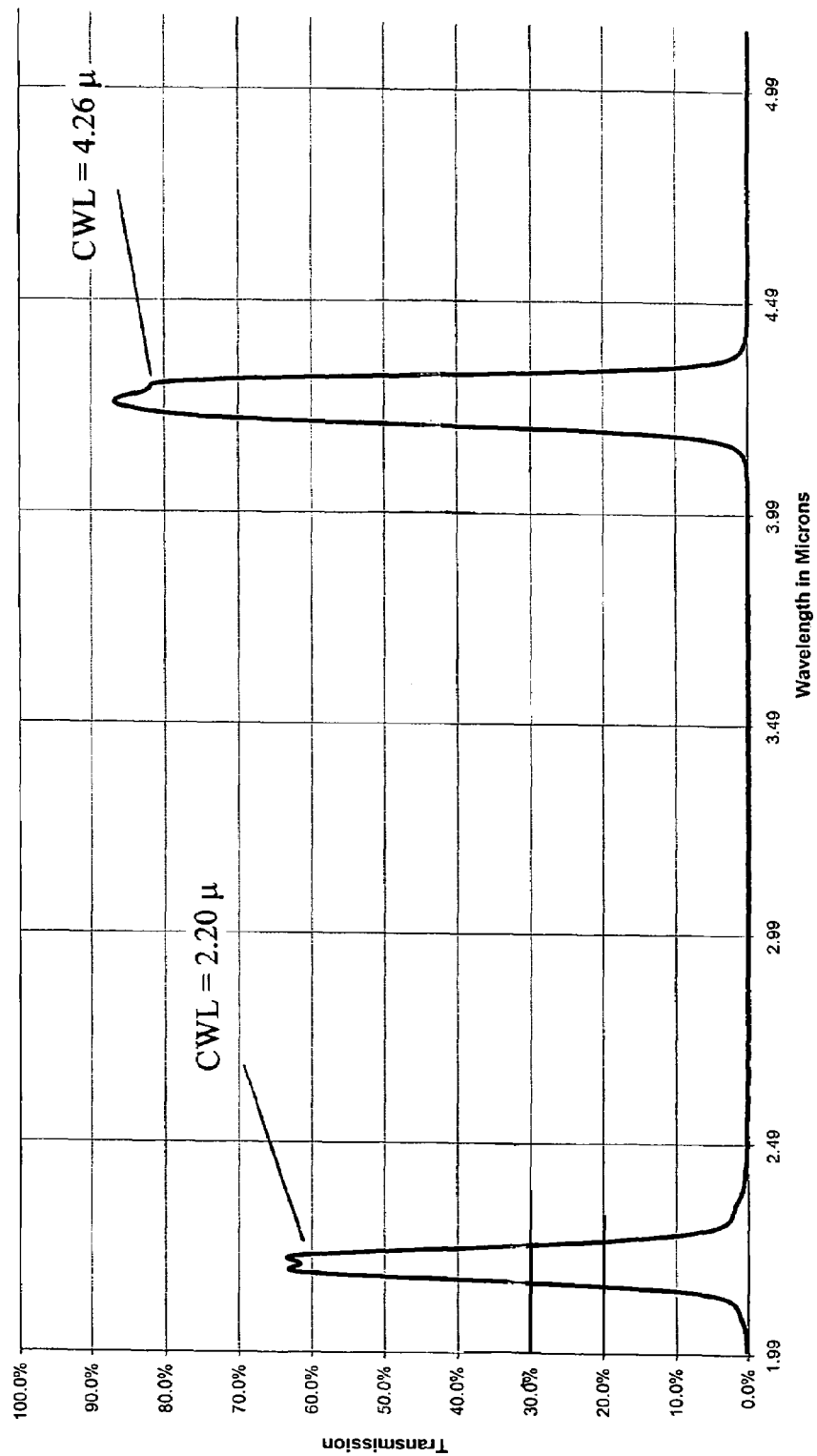
Figure 1. The spectral transmission curve for an actually fabricated dual passband filter (2.2 μ and 4.26 μ) for use with a single beam $CO_2$ NDIR sensor utilizing the currently invented methodology.

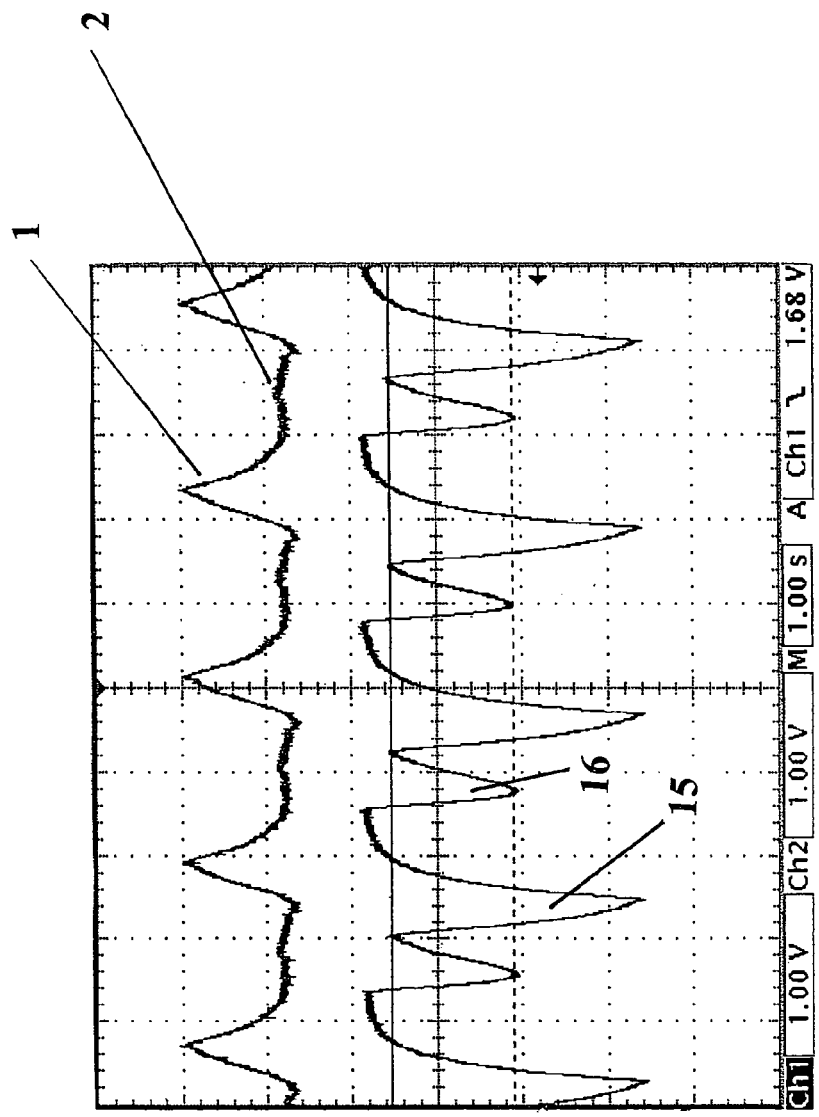
Figure 2. The large amplitude difference in the detector outputs as observed experimentally (upper trace) between the $T_H$ and the $T_L$ states. The same outputs for the two states (lower trace) after the currently invented real time programmable infrared source control is applied to the single detector circuit.

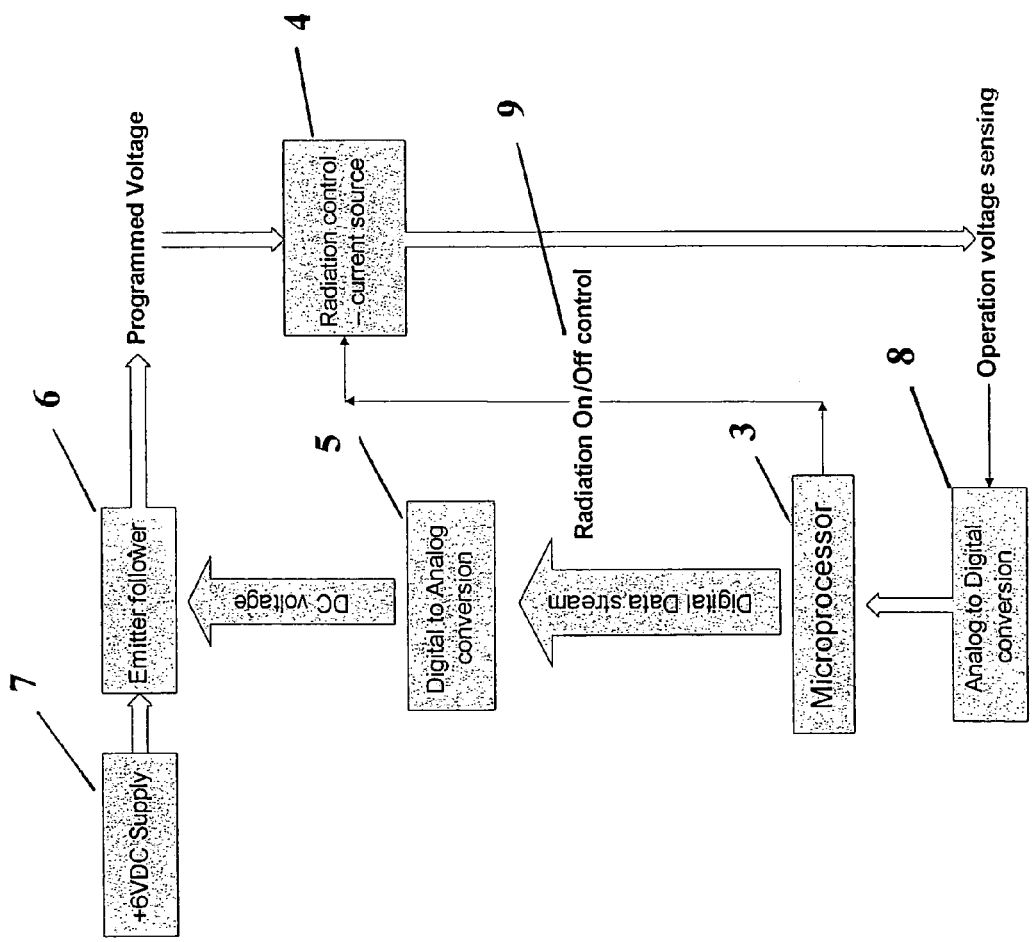
Figure 3. A schematic circuit illustrating the real time programmable infrared radiation source control.

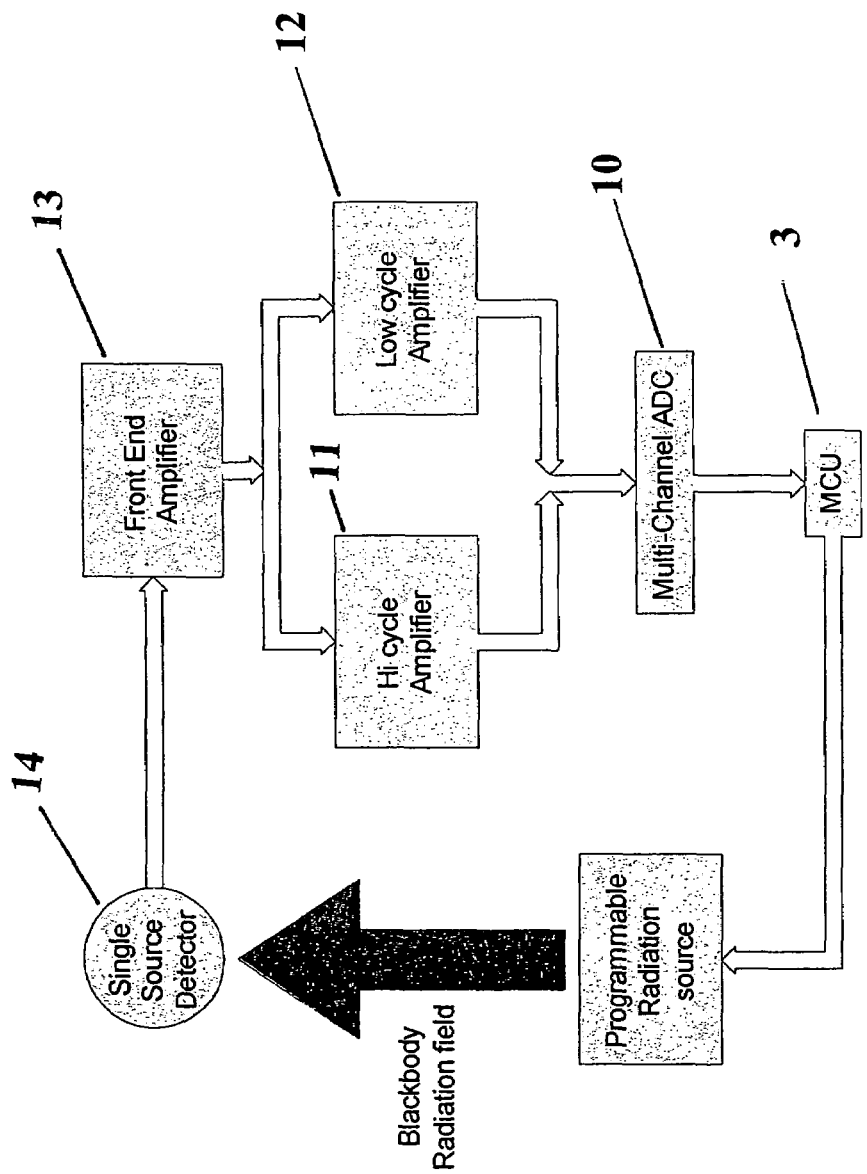
Figure 4. A schematic circuit illustrating the control of the radiation source via the synchronization of the detected high and low signals by the microprocessor in one 'AC' cycle using the multi-channel Analog-to-Digital converter chip.

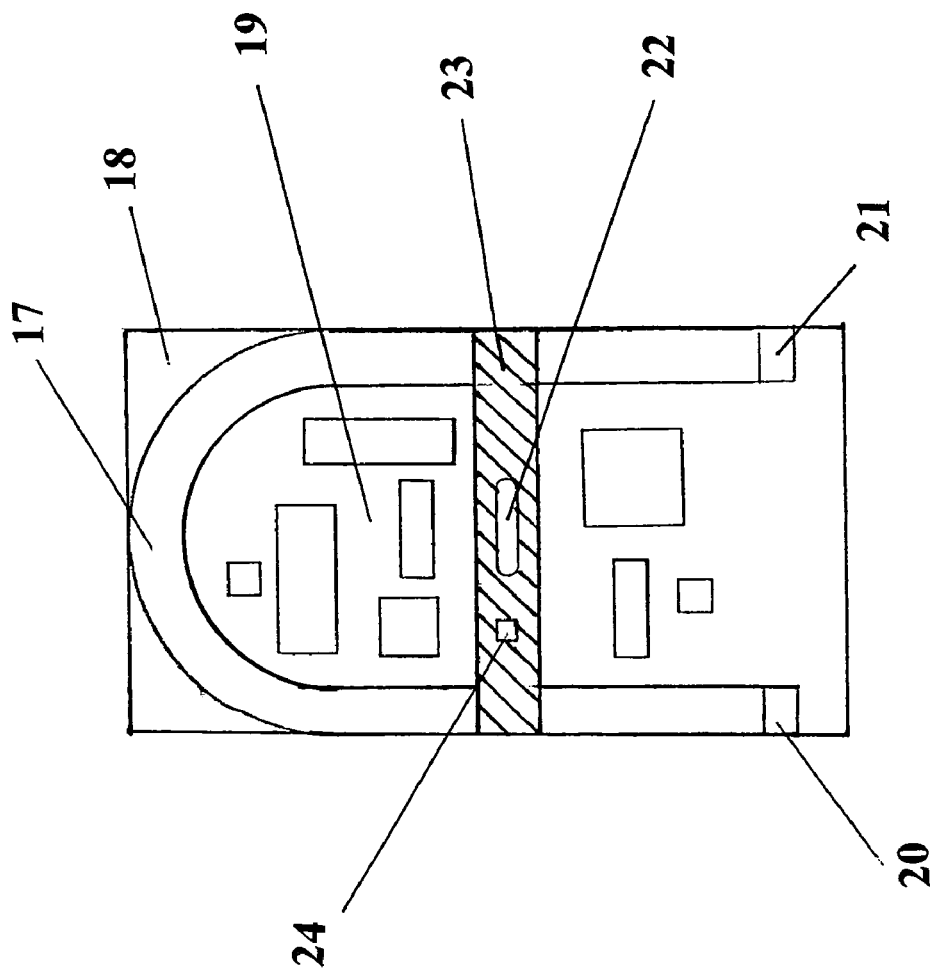
Figure 5. A schematic diagram illustrating the currently invented sample chamber configuration for controlling and regulating the temperature of the single beam sample chamber.

ULTRA LOW COST NDIR GAS SENSORS

FIELD OF THE INVENTION

The present invention generally relates to the field of gas sensing devices and, more particularly, to NDIR gas analyzers.

BACKGROUND OF THE INVENTION

Non-Dispersive infrared (NDIR) gas analyzers have been used for detecting the presence and concentration of various gases for over four decades. The NDIR technique has long been considered as one of the best methods for gas measurement. In addition to being highly specific, NDIR gas analyzers are also very sensitive, stable and easy to operate and maintain.

In contrast to NDIR gas sensors, the majority of other types of gas sensors today are in principle interactive. Interactive gas sensors are less reliable, generally nonspecific, and in some cases can be poisoned or saturated into a nonfunctional or irrecoverable state.

Despite the fact that interactive gas sensors are mostly unreliable and that the NDIR gas measurement technique is one the of best there is, NDIR gas analyzers have still not enjoyed widespread usage to date mainly because of the fact that their cost is still not low enough as compared to other inferior gas sensors for many applications.

In the past, NDIR gas analyzers typically included an infrared source, a motor-driven mechanical chopper to modulate the source, a pump to push or pull gas through a sample chamber, a narrow bandpass interference filter, a sensitive infrared detector plus expensive infrared optics and windows to focus the infrared energy from the source to the detector. In an attempt to reduce the cost and simplify the implementation of the NDIR methodology, a low-cost NDIR gas sensor technique was earlier developed. This low-cost NDIR technique employs a diffusion-type gas sample chamber of the type disclosed in U.S. Pat. No. 5,163,332, issued on Nov. 17, 1992 to Wong, one of the present applicants. This diffusion-type gas sample chamber eliminates the need for expensive optics, mechanical choppers and a pump for pushing or pulling the gas into the sample chamber. As a result, a number of applications using NDIR gas sampling technique, which were previously considered impractical because of cost and complexity, have been rendered viable ever since.

In the ensuing years since the U.S. Pat. No. 5,163,332 (1992) was issued, Wong, one of the present applicants, continued to refine and improve low-cost NDIR gas sampling techniques as evidenced by the issuance of U.S. Pat. No. 5,222,389 (June 1993), U.S. Pat. No. 5,341,214 (August 1994), U.S. Pat. No. 5,347,474 (September 1994), U.S Pat. No. 5,453,621 (September 1995), U.S. Pat. No. 5,502,308 (March 1996), U.S. Pat. No. 5,747,808 (May 1998), U.S. Pat. No. 5,834,777 (November 1998) and U.S. Pat. No. 6,237,575 (May 2001) to same. However, it has been quite apparent that despite the intense efforts over the years by Wong and others in the field, the unit sale price of NDIR gas sensors is still too high for many applications. It is of interest to note that back in 1991 and prior to the issuance of U.S. Pat. No. 5,163,332 (1992) to Wong, the same inventor has earlier advanced the concept of a simpler NDIR sensor methodology using spectral ratioing technique with a differential temperature infrared source in U.S. Pat. No. 5,026, 992 (1991). However, even after almost 15 years, this concept has to date neither been proven to be viable in theory nor has it been experimentally demonstrated to illustrate its practicality. It was found out only very recently and experimentally by Wong, the original inventor of U.S. Pat. No. 5,026,992 (1991) and one of the present applicants, that although the concept as suggested by the author was sound, the method does not work if the prescribed steps were followed exactly according to the teaching of the patent. Furthermore, it was found out by the present applicants that the methodology itself has to be completely reformulated taking into consideration the shortcomings of both the method and the system components as suggested by the original inventor.

There is still a long felt need in a variety of industries and applications to use lower cost NDIR gas sensors, and so far this desire has gone unanswered. It is this need that the current application seeks to address and bring about a new and novel technique for the design and implementation for ultra low cost NDIR gas sensors.

SUMMARY OF THE INVENTION

The present invention relies upon a single beam NDIR gas sensor for detecting the concentration of a gas species in a sample chamber with a differential infrared source element that can produce radiation having a first spectrum when its temperature is at a first high temperature and a second spectrum when its temperature is at a second lower temperature, a detector for generating a detector output and a dual pass band filter located between the source element and the detector. The present invention is generally directed to such an NDIR gas sensor which also includes a driver for driving the source at either the first or the second temperature, a feed back loop to sense an operation voltage of the source, a differential gain amplifier for creating a high cycle amplified output during a high cycle and a low cycle amplified output during a low cycle, and a controller for synchronizing the driver so that the source is driven at the first temperature and a high cycle amplification is applied to the detector output during the high cycle and the source is driven at the second temperature and a low cycle amplification is applied to the detector output during the low cycle while a signal processor determines the concentration of the gas species through use of the high cycle amplified output and the low cycle amplified output.

In a separate aspect of the present invention, the concentration of a gas species is determined by such an improved NDIR gas sensor by the steps of driving the source element at a first high temperature and then applying a high cycle amplification to the detector output to create a high cycle amplified output, driving the source element at a second low temperature and than applying a low cycle amplification to the detector output to create a low cycle amplified output and determining the concentration of the gas species through use of the high cycle amplified output and the low cycle amplified output.

In another separate aspect of the present invention, a single beam NDIR gas sensor uses a thermally insulated tube sample chamber, an incandescent miniature light bulb with a filament surrounded by a glass envelope secured at a first end of the sample chamber, a single infrared detector secured at a second end of the sample chamber, a dual bandpass filter (having a neutral passband and an absorption passband for the gas species) mounted at the single infrared detector between the bulb and the detector, a controlled heater secured to the tube for maintaining the sample chamber at a preselected temperature greater than an ambient temperature when the sensor is turned on, a driver for the bulb with a high input power level and a low input power level so that the bulb will emit radiation at first and second voltage outputs characterized by two corresponding Planck curves dependent upon temperatures, a feed back loop to sense an operation voltage of the bulb, a differential gain amplifier for creating a high cycle amplified output during a high cycle and a low cycle amplified output during a low cycle, a controller for synchronizing the driver so that the bulb is driven at the high input power level and a high cycle amplified gain is applied to the detector output during the high cycle and the bulb is driven at the low input power level and a low cycle amplified gain is applied to the detector output during the low cycle and a signal processor for determining the concentration of the gas species through use of the high cycle amplified output and the low cycle amplified output.

In a related but still separate aspect of the present invention, a single beam NDIR gas sensor such as was just described is used to detect the concentration of a gas species by heating the sample chamber to a preselected temperature greater than an ambient temperature and maintaining the sample chamber at the preselected temperature, driving the bulb at a first high voltage input and then applying a high cycle amplification to the detector output to create a high cycle amplified output, driving the bulb at a second low voltage input and than applying a low cycle amplification to the detector output to create a low cycle amplified output and then determining the concentration of the gas species through use of the high cycle amplified output and the low cycle amplified output. In addition, a feed back loop can be used to sense the operation voltage of the bulb while the bulb is synchronized so that it is driven at the first high voltage input and the high cycle amplified output is applied to the detector output during a high cycle and the bulb is driven at the second low voltage input and the low cycle amplified output is applied to the detector output during a low cycle.

In still a further group of aspects of the present invention, the glass envelope of the incandescent miniature light bulb used in the single beam NDIR gas sensor is maintained at an equilibrium temperature (such as approximately 30 degrees Celsius) during the low cycle operation state by the controlled heater, the equilibrium temperature is a constant temperature that varies by less than two degrees Celsius while the ambient temperature is 22 degrees Celsius, and the glass envelope of the incandescent miniature light bulb is the primary radiation emitter during the low cycle.

In yet a further group of aspects of the present invention, the single beam NDIR gas sensor sample chamber is secured to a first side of a printed circuit board, the signal processing circuit components are mounted on a second side of the printed circuit board, an insulated aluminum tube sample chamber is configured with at least one substantial U-bend and a casing surrounds the printed circuit board.

Accordingly, it is an object of the present invention to bring forth a new and novel sensor concept for the realization of the long sought after ultra low cost NDIR gas sensor.

This and further objects and advantages will be apparent to those skilled in the art in connection with the drawings and the detailed description of the preferred embodiment set forth below.

BRIEF DESCRIPTION OF THE DRAWINGS

FIG. 1. The spectral transmission curve for an actually fabricated dual passband filter (2.2μ and 4.26μ) for use with a single beam CO2 NDIR sensor utilizing the currently invented methodology.

FIG. 2. The large amplitude difference in the detector outputs as observed experimentally (upper trace) between the $T_H$ and the $T_L$ states. The same outputs for the two states (lower trace) after the currently invented real time programmable infrared source control is applied to the single detector circuit.

FIG. 3. A schematic circuit illustrating the real time programmable infrared source control.

FIG. 4. A schematic circuit illustrating the control of the radiation source via the synchronization of the detected high and low signals by the microprocessor in one 'AC' cycle using the multi-channel Analog-to-Digital converter chip.

FIG. 5. A schematic diagram illustrating the currently invented sample chamber configuration for controlling and regulating the temperature of the single beam sample chamber.

DETAILED DESCRIPTION OF THE INVENTION

The most prevalent NDIR gas sensor today is a dual beam device having a signal and a reference beam implemented with a single infrared source and two separate infrared detectors, each having a different interference filter. The signal filter contains a narrow spectral passband that allows radiation relevant to the absorption of the gas to be detected to pass. Thus the presence of the gas of interest will modulate the signal beam. The reference filter contains a narrow spectral passband that is irrelevant to the gas in question and also to all the common gases present in the atmosphere. Therefore the reference beam will stay constant and act as a reference for the detection of the designed gas species over time. Although the dual beam technique works well for a host of applications, especially with the detection of relatively low concentrations of carbon dioxide (CO2) gas (400-2,000 ppm) for HVAC (Heating, Ventilation and Air Conditioning) and IAQ (Indoor Air Quality) applications, the cost of the sensor is limited by the expensive detector package which contains two detectors each equipped with a different interference filter. Furthermore, the dual beam NDIR gas sensor still has a number of shortcomings that require special treatments in order to render the sensor adequately reliable and stable over time. These shortcomings include the aging of the infrared source which might cause the spatial distribution of infrared radiation reaching the detectors to change; the same applies to the non-uniform aging of the inner reflective surfaces of the sample chamber affecting the spatial distribution of the impinging radiation at the detector assembly, the different aging characteristics for the two interference filters each being manufactured via different deposition processing steps and materials and finally the potential aging characteristics for the two detectors to change differently.

In order to improve the performance and cost of the ever more popular dual beam NDIR gas sensor, one has to seek favorable opportunities in the detector assembly end of this class of sensors. Needless to say, if one can reduce the number of detectors from two to one which in effect reduces the dual beam technique into a single beam one, while at the same time render this new technique adequately workable for an accurate, reliable and stable NDIR gas sensor, then the goal of achieving an ultra low cost sensor might become viable.

The first task at hand is to find out how to create spectrally and functionally a dual beam situation with only a single infrared source and a single detector. One conclusion is that we will be able to do very little with the infrared detectors and the interference filters which the dual beam sensor carries because they are passive components. Therefore, one approach is to do something with the infrared source which is an active component. As observed in U.S. Pat. No. 5,026,992 (1991) issued to Wong, one can change the spectral characteristic output of the source according to the Planck's radiation curves by driving it at different power levels so as to assume different blackbody temperatures at different times. This can in fact be readily achieved since one has to pulse the infrared source anyway as in the dual beam technique. By so doing it is possible to create two beams with different spectral characteristics for the source. However, how would the detector respond differently to these two beams? Again by observing U.S. Pat. No. 5,026,992 (1991) mentioned earlier, one can resort to the use of a dual passband interference filter with one of the spectral bands relevant to the gas to be detected and the other simply a reference or neutral band. Thus, at least in concept, as advanced in the earlier cited patent, with the use of a single detector carrying a dual passband filter and by driving the infrared source at two different power levels, one should theoretically be able to derive information about the gas in question by calibrating the ratio of the outputs for the two beams with the concentration levels for the gas, very much like the way for a conventional dual beam NDIR gas sensor.

While this thinking approach to achieve our goal at hand appears sound in concept, it is a totally different story when it comes to carrying it out in practice. This method simply does not work even when using a genuine blackbody source which assumes only one single temperature when driven at one particular power level and radiates according to one unique Planck curve. It was recently found out experimentally that in order for this method to be able to detect low to medium concentrations of gas, e.g. 400-2,000 ppm of CO2 with a resolution of +/−50 ppm, and even with a sample pathlength of 8 inches (longer than what is usually needed for a conventional dual beam sensor), the power levels needed to drive the infrared source in order to create two adequate and spectrally different beams have to differ by more than a factor of 20. In other words, the low power driven beam has such a small generated signal at the detector that it cannot be readily processed by any reasonably designed processing electronics.

One potential solution to this problem is to increase the gain of the amplifier stages following the detector. However, this is not feasible as we have created in reality just a single beam with a single set of processing electronics. Since the two spectral beams created with the use of only one source and one detector will in essence be processed by the same signal electronics, arbitrarily increasing the gain of the amplifier stages will no doubt render the low power beam signal more amenable to processing but will also send the high power beam signal to the rail (exceeding voltage supply limits). Unless some novel signal processing approach is advanced as by the present invention, such an approach will simply not work.

Another potential solution to this problem is to shift the driving power ratio to higher blackbody temperatures in order to increase the low power beam signal at the detector. Unfortunately, unlike the tungsten filament of a miniature light bulb, which can be driven to temperatures in excess of 2,000° C., genuine blackbody sources with temperatures above 750° C. simply are not readily available unless they are custom fabricated and consequently carry a very high unit cost. Therefore the approach of operating the infrared source at a higher temperature ratio using a genuine blackbody source is inconsistent with the goal of trying to develop an ultra low cost NDIR gas sensor and thus is not cost-wise logical.

Even if we could somehow make the conventional genuine blackbody source work with the currently proposed single detector approach, the cost for a genuine blackbody source might still be prohibitively high so as to render the proposed approach impractical. Since the goal of the present invention is to bring forth a novel approach of using just one infrared source and one infrared detector for achieving the goal of implementing an ultra low cost NDIR gas sensor, such a technique must also be made to work with a non-genuine blackbody source, such as a much lower cost miniature incandescent light bulb.

The present invention advances a novel single beam methodology, with the use of a low cost non-genuine blackbody source such as an incandescent light bulb, and an infrared detector equipped with a dual passband interference filter. In order to overcome the signal processing difficulty in the handling of two beam signals with a vast amplitude discrepancy, a novel real time programmable infrared source control technique is advanced. Such a technique enables the common signal processing electronics for the detector to attain a synchronized multiple amplifier gain capability for two or more output power states from the infrared source. The present invention further advances a novel sample chamber configuration for the sensor in order to render the use of a non-genuine blackbody source, in lieu of a genuine blackbody source, for successfully using a single beam methodology for the implementation of an ultra low cost NDIR gas sensor.

As mentioned earlier, the concept advanced in U.S. Pat. No. 5,026,992 calls for operating a genuine blackbody source alternately at a high emission temperature state, $T_H$, and then at a low emission temperature state, $T_L$, in order to shift the spectral content of the source. The theoretical example for the detection of methane using this methodology as cited in said patent uses $T_H$ and $T_L$ equal to 723° K. and 523° K. respectively which provides a 1.0% change in the calculated output signal ($R_s$ or the voltage ratio for the $T_H$ and $T_L$ states) for detecting a level of 10,000 ppm of methane. Even in this theoretical example, the output for state $T_H$ can be calculated using Planck's curves to be more than 11 times the output for the state $T_L$. In this simulated calculation, a genuine blackbody source having an area of ~2 mm×2 mm is used together with the characteristics for the dual passband filter (2.20μ and 3.40μ) as suggested in the patent mentioned above and a standard thermopile detector having a typical responsibility of ~200 V/W. In order to demonstrate experimentally an even more difficult disposition for the detection of CO2 gas, an actual dual bandpass filter having Center Wavelengths (CWL's) at ~2.20μ and ~4.23μ respectively was procured as depicted in FIG. 1. Using a 1.5 mm×1.5 mm thick film resistor fabricated on an 10 mils thick alumina substrate as a genuine blackbody source and the dual passband filter as shown in FIG. 1 mounted on a 1 mm×1 mm thermopile detector can (TO-18), the voltage outputs at the detector for driving the genuine infrared source at 750° C. ($T_H$ state) and 300° C. ($T_L$ state) respectively are shown in FIG. 2. It can be seen from FIG. 2 (upper trace) that the voltage amplitude for the $T_H$ state 1 is almost an order of magnitude greater than the voltage amplitude for the $T_L$ state 2, thus practically demonstrating the difficulty in the implementation of the single beam NDIR gas sensor concept as advanced in U.S. Pat. No. 5,026,992 (1991).

For a methane single beam NDIR gas sensor requiring a much higher resolution such as 100 ppm, e.g., the source temperature for the low emission state has to be much lower than 523° K. in order for it to work properly. The resultant discrepancy between the output voltages for states $T_H$=723° K. and $T_L$=323° K. is estimated to be 50 times or more. This creates an extraordinarily difficult situation for the design of a single signal processing circuit serving both the $T_H$ and $T_L$ output states from one and the same infrared detector. An adequate amplifier gain for the $T_L$ output state would easily increase the output level for the $T_H$ state to exceed the voltage supply limit thus rendering the signal processing circuitry effectively nonfunctional.

In order to overcome this difficulty in the design of a suitable signal processing circuit for this differential source temperature single beam NDIR sensor concept, the present inventors advance the methodology of a real time programmable infrared source control for attaining a synchronized multiple amplifier gain capability for two or more output states from a single detector. Such a control is shown schematically in FIG. 3.

As shown in FIG. 3, one can see that as many as three feedback loops are operating simultaneously between the microprocessor 3 and the Radiation control—current source 4. At a particular point in time, the digital data stream from microprocessor 3 is routed through a Digital to Analog conversion chip 5 in order to generate a programmed DC voltage to drive the Radiation control—current source 4 with the help of the Emitter Follower 6 and Voltage Supply 7. The correct adjustment of the programmed voltage for the source is determined by the use of a feedback loop to sense the operation voltage of the source which is then converted using Analog to Digital converter 8 before returning back to the microprocessor 3. Meanwhile it is the microprocessor 3 that generates a Radiation ON/OFF control signal 9 for synchronizing (or alternating) the correct programmed voltages for operating both the $T_H$ and the $T_L$ source emission states. In summary, the High and Low signals detected in one "AC" cycle are synchronized by the microprocessor 3 to control the radiation source 4 and the multi-channel ADC 10 simultaneously as shown in more detail in FIG. 4.

As shown in FIG. 4, the microprocessor 3 detects the High and Low signals from the Multi-Channel ADC 10 fed by both the Hi cycle amplifier 11 and Low cycle amplifier 12 from the front end amplifier 13 generated by the single source detector 14. By processing these signals every AC cycle, the microprocessor 3 is able to synchronize the two different voltage levels applied to just one single radiation source. Furthermore, the different gain factors applied to the Hi and Low cycle amplifiers are also correctly applied to the signals detected during the High and Low cycles thereby eliminating the possibility that the voltage level for the High cycle (or $T_H$) may exceed the supply voltage limit. This operational feature is illustrated in FIG. 2 (lower trace) when applied to the experimentally implemented single beam CO2 sensor using an actual dual passband filter. As one can see in FIG. 2 (lower trace), the amplified voltage for the $T_H$ state 15 and the amplified voltage for the $T_L$ state 16 which correspond respectively to the non-amplified voltages 1 and 2 (upper trace) are both in range despite their great discrepancy in the pre-amplified signal levels.

The differential temperature source concept for implementing a single beam NDIR gas sensor as disclosed in U.S. Pat. No. 5,026,992 (1991) calls for the use of a genuine blackbody source. In other words, the suggested infrared source to be used must behave precisely like a blackbody with its output or spectral radiant emittance, $M_\lambda$, uniquely determined by a single source temperature as prescribed by the well-known Planck's Law. As alluded to earlier, the use of genuine blackbody sources that are available today might still be too cost limiting contrary to the ultra low cost goal that the current applicants are trying to achieve. For the past two decades, the use of very low cost miniature incandescent light bulbs as non-genuine but practical infrared sources for NDIR gas sensors, including the dual beam sensor types, has gained worldwide acceptance. The cost advantage for the ultra low cost single beam NDIR sensor could be significant if a non-genuine blackbody source like the incandescent light bulb could be utilized in lieu of a genuine blackbody one.

The reason why incandescent light bulbs are considered as non-genuine blackbody sources can be explained as follows. Typically an incandescent miniature light bulb has a tungsten filament packaged in vacuum surrounded by a glass envelope. When the light bulb is used as a pulsating infrared source, the tungsten filament will be turned alternately on and off. The tungsten filament taken alone is a genuine blackbody source emitting radiation in all wavelengths long and short dependent upon its operating temperature. Meanwhile the spectral transmission characteristic of the glass envelope has a sharp cutoff somewhere between 3 and 4.5 microns. Thus some of the long wavelength radiation emitted by the tungsten filament will be absorbed by the envelope resulting in a rapid rise in temperature when the tungsten filament is turned on. After some operation time has elapsed, the tungsten filament and the bulb envelope will come to a thermal equilibrium. The net result is that in addition to the tungsten filament acting as a high temperature infrared source (a genuine blackbody) for the incandescent light bulb, the bulb envelope also behaves as a second infrared source albeit at a much lower temperature. But since the effective area of the bulb envelope is very much larger than that for the tungsten filament, its contribution to the total radiation output for the light bulb as an infrared source could be comparable to that of the tungsten filament itself. The resultant spectral output of an incandescent light bulb is therefore a spectral convolution of the two separate sources, namely the tungsten filament and the bulb envelope. For this reason the incandescent light bulb is technically considered as a non-genuine blackbody source since it is not uniquely characterized by just one single source temperature.

No teaching or suggestion can be found in U.S. Pat. No. 5,026,992 (1991) as to how the spectral ratioing differential source temperature concept might work or not work for a single beam NDIR sensor if a non-genuine blackbody is used in lieu of a genuine one as the infrared source. However, in order to achieve the goal of being able to manufacture an ultra low cost single beam NDIR sensor using this method, the present authors advance a novel sample chamber configuration for the sensor in order that a non-genuine blackbody source, in this case an incandescent miniature light bulb, can work successfully. As discussed earlier, in order to make the source differential temperature concept work one must create enough spectral contrast between the $T_H$ and the $T_L$ states. An efficacious way to accomplish this, like in the case for using a genuine blackbody as the infrared source, is to operate the $T_L$ state at as low a temperature as possible.

When a miniature incandescent light bulb is used as the infrared source, the temperature of the light bulb envelope becomes the primary radiation emitter for the $T_L$ state. This is due to the fact that the temperature of the filament during $T_L$ is very low (typically 300-400° K.) and the area of the filament is also very small when compared with the effective area of the light bulb envelope (~100 times less). Furthermore, the light bulb envelope, being made out of glass, is absorbing a lot of long-wavelength radiated energy from the hot filament when it is in the $T_H$ state. Some of the absorbed heat persists to the immediately following $T_L$ state. Unfortunately this situation creates a serious problem for the sensor operation. The reason is that when the sensor is operating at or above room temperature, no problem arises because in the $T_L$ state, the light bulb envelope does not lose much heat to the environment and continues to retain its relatively high temperature as a radiation emitter. However, when the operating temperature of the sensor is below room temperature, the envelope starts to lose its efficacy as an efficient radiation emitter due to the rapid loss of heat from its emitting surface to the environment. When the operating temperature of the sensor approaches 0° C. or below, the light bulb envelope as an infrared source is virtually shut down because of the fact that its temperature will approach 0° C. or lower and therefore cease to be an effective infrared source for the single beam sensor.

The current invention advances a simple sample chamber configuration for the single beam sensor in order to cope with this potential problem by first designing the sample chamber in the form of an insulated U-bend shape tube 17 (insulation not shown) about 6 inches long and made out of aluminum, which is a good thermal conductor, as illustrated in FIG. 5. An aluminum strut or beam 23 which houses a 3-watt wire-wound resistor 22 as a heater and a thermistor 24 for monitoring its temperature thermally connects the middle sections of the two ends of the U-tube as shown in FIG. 5. The entire insulated sample chamber configuration including the U-tube sample chamber 17, the heater strut 23, the miniature incandescent light bulb 20 mounted at one end of the U-tube and the infrared detector 21 mounted at the other end is secured with hardware to one side of a printed circuit board (PCB) 18. The signal processing circuit components are mounted on the other side of the PCB 18.

The heater strut 23 serves to regulate the temperature of the entire insulated aluminum sample chamber configuration 17 to an elevated temperature above ambient at all times when the sensor is first turned on. This sample chamber configuration 17 with the strategically located heater strut 23 prevents the loss of heat from the light bulb envelope in the $T_L$ state to the ambient, even when the temperature of the latter falls below 0° C. This novel configuration enables the single beam NDIR sensor to operate properly at all ambient temperatures. The sample chamber configuration 17 works both for the diffusion sampling mode and for the flow through sampling mode. In the former case, small holes located diagonally in pairs are drilled along the insulated U-bend tube approximately one half inch apart for the sampled air to freely diffuse through the sample chamber for detection. In the latter case two miniature hose fittings are secured one at each end of the U-tube sample chamber so that air can be pushed through or pulled through the sample chamber for detection as desired. Finally the entire PCB 18 housing the single beam NDIR gas sensor can be fitted into any plastic casing with appropriate dimensions as desired.

Thus, there has been described a methodology using a real time programmable blackbody radiation source control circuit for successfully implementing a differential source temperature single beam NDIR gas sensor. Furthermore, a novel sample chamber configuration is advanced in order to enable the use of a non-genuine blackbody source for successfully implementing a differential source temperature single beam NDIR gas sensor.

While the invention has been described herein with reference to certain examples, those examples have been presented for illustration and explanation only, and not to limit the scope of the invention. Additional modifications and examples thereof will be obvious to those skilled in the art having the benefit of this detailed description. Further modifications are also possible in alternative embodiments without departing from the inventive concept.

Accordingly, it will be apparent to those skilled in the art that still further changes and modifications in the actual concepts described herein can readily be made without departing from the spirit and scope of the disclosed inventions as defined by the following claims.

What is claimed is:

1. In a single beam NDIR gas sensor for detecting the concentration of a gas species in a sample chamber with a differential infrared source element that can produce radiation having a first spectrum when its temperature is at a first high temperature and a second spectrum when its temperature is at a second lower temperature, a detector for generating a detector output and a dual pass band filter located between the source element and the detector, the improvement of which comprises:
   a driver for driving the source at either the first or the second temperature;
   a feed back loop to sense an operation voltage of the source;
   a differential gain amplifier for creating a high cycle amplified output during a high cycle and a low cycle amplified output during a low cycle;
   a controller for synchronizing the driver so that the source is driven at the first temperature and a high cycle amplification is applied to the detector output during the high cycle and the source is driven at the second temperature and a low cycle amplification is applied to the detector output during the low cycle; and
   a signal processor for determining the concentration of the gas species through use of the high cycle amplified output and the low cycle amplified output.

2. A method for detecting the concentration of a gas species from a single beam NDIR gas sensor having a differential infrared source element that can produce radiation having a first spectrum when its temperature is driven by a driver at a first low temperature and a second spectrum when its temperature is driven by the driver at a second higher temperature, a detector for generating a detector output and a dual pass band filter located between the source element and the detector, comprising the steps of:
   driving the source element at a first high temperature-and then applying a high cycle amplification to the detector output to create a high cycle amplified output;
   driving the source element at a second low temperature and than applying a low cycle amplification to the detector output to create a low cycle amplified output; and
   determining the concentration of the gas species through use of the high cycle amplified output and the low cycle amplified output.

3. A single beam NDIR gas sensor for detecting the concentration of a gas species, comprising:
   a thermally insulated tube sample chamber;
   an incandescent miniature light bulb with a filament surrounded by a glass envelope secured at a first end of the sample chamber;
   a single infrared detector secured at a second end of the sample chamber;

a dual bandpass filter mounted at the single infrared detector between the bulb and the detector, said dual bandpass filter having a neutral passband and an absorption passband for the gas species;

a controlled heater secured to the tube for maintaining the sample chamber at a preselected temperature greater than an ambient temperature when the sensor is turned on;

a driver for the bulb with a high input power level and a low input power level so as to render said bulb into emitting at a first voltage output and a second voltage output whose radiation outputs are characterized by two corresponding Planck curves dependent upon temperatures;

a feed back loop to sense an operation voltage of the bulb;

a differential gain amplifier for creating a high cycle amplified output during a high cycle and a low cycle amplified output during a low cycle;

a controller for synchronizing the driver so that the bulb is driven at the high input power level and a high cycle amplified gain is applied to the detector output during the high cycle and the bulb is driven at the low input power level and a low cycle amplified gain is applied to the detector output during the low cycle; and a signal processor for determining the concentration of the gas species through use of the high cycle amplified output and the low cycle amplified output.

4. The sensor of claim 3, wherein the glass envelope is maintained at an equilibrium temperature during the low cycle operation state by the controlled heater.

5. The sensor of claim 4, wherein the ambient temperature is 22 degrees Celsius.

6. The sensor of claim 3, wherein the equilibrium temperature is a constant temperature that varies by less than two degrees Celsius.

7. The sensor of claim 3, wherein the sample chamber is secured to a first side of a printed circuit board.

8. The sensor of claim 7, wherein the signal processing circuit components are mounted on a second side of the printed circuit board.

9. The sensor of claim 3, wherein the preselected temperature is approximately 30 degrees Celsius.

10. The sensor of claim 9, wherein the glass envelope is the primary radiation emitter during the low cycle.

11. The sensor of claim 3, wherein the insulated tube sample chamber is comprised of aluminum.

12. The sensor of claim 11, wherein the insulated tube sample chamber is comprised with at least one substantial U-bend.

13. The sensor of claim 12, further comprising a casing which surrounds the printed circuit board.

14. A method for detecting the concentration of a gas species from a single beam NDIR gas sensor having a thermally insulated tube sample chamber, an incandescent miniature light bulb with a filament surrounded by a glass envelope secured at a first end of the sample chamber, a single infrared detector secured at a second end of the sample chamber, a dual bandpass filter mounted at the single infrared detector between the bulb and the detector, said dual bandpass filter having a neutral passband and an absorption passband for the gas species, and a controlled heater secured to the tube, comprising the steps of:

heating the sample chamber to a preselected temperature greater than an ambient temperature and maintaining the sample chamber at the preselected temperature;

driving the bulb at a first high voltage input and then applying a high cycle amplification to the detector output to create a high cycle amplified output;

driving the bulb at a second low voltage input and than applying a low cycle amplification to the detector output to create a low cycle amplified output; and determining the concentration of the gas species through use of the high cycle amplified output and the low cycle amplified output.

15. The method of claim 14, comprising the further step of using a feed back loop to sense an operation voltage of the bulb and synchronizing the bulb so that it is driven at the first high voltage input and the high cycle amplified output is applied to the detector output during a high cycle and the bulb is driven at the second low voltage input and the low cycle amplified output is applied to the detector output during a low cycle.

16. The method of claim 14, wherein the ambient temperature is 22 degrees Celsius.

17. The method of claim 16, wherein the preselected temperature is approximately 30 degrees Celsius.

18. The method of claim 14, wherein the glass envelope is the primary radiation emitter at the second low voltage input.

* * * * *